United States Patent [19]

Saito et al.

[11] 4,189,476

[45] Feb. 19, 1980

[54] COMBATING PESTS WITH O,S-DIALKYL-O-HALOALKYL-PHOSPHOROTHIOLATES

[75] Inventors: Junichi Saito, Tokyo; Akio Kudamatsu, Kanagawa; Toyohiko Kume; Shinichi Tsuboi, both of Tokyo, all of Japan

[73] Assignee: Nihon Takushu Noyaku Seizo K.K., Tokyo, Japan

[21] Appl. No.: 916,164

[22] Filed: Jun. 16, 1978

[30] Foreign Application Priority Data

Jul. 25, 1977 [JP] Japan .................................. 52/88352

[51] Int. Cl.$^2$ .......................... A01N 9/36; C07F 9/165
[52] U.S. Cl. .................................... 424/224; 260/955; 260/963
[58] Field of Search ................. 260/955, 963; 424/224

[56] References Cited

U.S. PATENT DOCUMENTS 3,184,377  5/1965  Hensel et al. ........................ 424/224

FOREIGN PATENT DOCUMENTS 107581  8/1974  German Democratic Rep. ...... 260/963

OTHER PUBLICATIONS

English translation of Japanese patent application 101131/76.

*Primary Examiner*—Anton H. Sutto
*Attorney, Agent, or Firm*—Sprung, Felfe, Horn, Lynch & Kramer

[57] ABSTRACT

O,S-Dialkyl-O-haloalkyl-phosphorothiolates of the formula

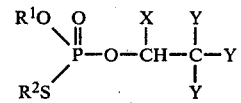

in which
 $R^1$ is alkyl with 1–8 carbon atoms,
 $R^2$ is alkyl with 1–8 carbon atoms or alkoxyalkyl with 2–8 carbon atoms,
 X is hydrogen, halogenoalkyl with 1–8 carbon atoms or alkoxy with 1–8 carbon atoms, and
 Y is halogen, which possess insecticidal, acaricidal and nematocidal properties.

14 Claims, No Drawings

COMBATING PESTS WITH O,S-DIALKYL-O-HALOALKYL-PHOSPHOROTHIOLATES

The present invention relates to and has for its objects the provision of particular new O,S-dialkyl-O-haloalkyl-phosphorothiolates which possess insecticidal, acaricidal and nematocidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

East German Patent No. 107581 discloses that organophosphoric acid esters of the general formula

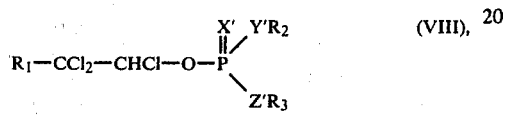

in which
R₁ represents chlorine or monochloromethyl,
R₂ represents alkyl,
R₃ represents alkyl, cycloalkyl, alkenyl, alkynyl, aryl or aryl carrying one or more substituents selected from alkyl, aryl, halogen, nitro, cyano, alkoxy and alkylmercapto substituents, and
X', Y' and Z' each represent oxygen or sulphur, have insecticidal and acaricidal activities.

Furthermore, published Japanese patent application No. 101131/76 discloses that organophosphoric acid esters of the general formula

in which
R represents lower alkyl,
A represents lower alkyl, cycloalkyl or halogenoalkyl, and
B represents lower alkyl or halogenoalkyl, provided that A and B do not represent identical alkyl radicals,
have a fungicidal activity when used by water-surface application.

The present invention now provides, as new compounds, the organophosphoric acid esters of the general formula

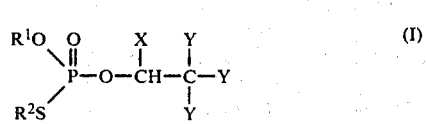

in which
R¹ represents alkyl with 1–8 carbon atoms,
R² represents alkyl with 1–8 carbon atoms or alkoxyalkyl with 2–8 carbon atoms,
X represents hydrogen, halogenoalkyl with 1–8 carbon atoms or alkoxy with 1–8 carbon atoms, and
Y represents halogen.

The compounds of the formula (I) have been found to have excellent insecticidal, acaricidal and nematocidal activities.

Preferably, R¹ represents alkyl with 1–3 carbon atoms (especially methyl, ethyl or n-propyl), R² represents alkyl with 3 or 4 carbon atoms (especially n-propyl, n-butyl, sec.-butyl or isobutyl) or alkoxyalkyl with 3–6 carbon atoms (especially 2-(C₁–C₄-alkoxy)ethyl such as methoxyethyl, ethoxyethyl, propoxyethyl, isopropoxyethyl or n-butoxyethyl), X represents hydrogen, trihalogenomethyl (especially trichloromethyl or trifluoromethyl) or alkoxy with 1–4 carbon atoms (especially ethoxy), and Y represents fluorine or chlorine.

The present invention also provides a process for the preparation of a compound of the formula (I), in which
(a) a thiophosphoryl halide of the general formula

in which
R¹ and R² have the meanings stated above, and
Hal represents halogen,
is reacted with an alcohol or alcoholate of the general formula

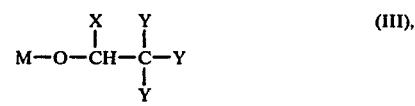

in which
X and Y have the meanings stated above, and
M represents hydrogen or an alkali metal, or
(b) a thiophosphoryl halide of the general formula

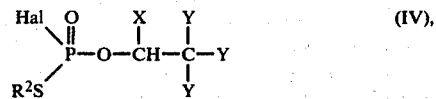

in which
R², X and Y have the meanings stated above, and
Hal represents halogen,
is reacted with an alcohol or alcoholate of the general formula

in which
R¹ has the meaning stated above, and
M represents hydrogen or an alkali metal, or
(c) a phosphite of the general formula

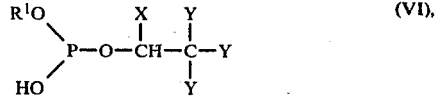

in which
R¹, X and Y have the meanings stated above, is reacted with a sulfenyl halide of the general formula

in which

R² has the meaning stated above, and

Hal represents halogen.

Specific examples of the thiophosphoryl halides of the general formula (II), used as starting materials in process variant (a), are O-methyl-S-n-propylphosphorochloride thiolate, O-ethyl-S-n-propylphosphorochloride thiolate, O,S-di-n-propylphosphorochloride thiolate, O-ethyl-S-n-butylphosphorochloride thiolate, O-ethyl-S-isobutylphosphorochloridethiolate, O-ethyl-S-sec.-butyl-phosphorochloridethiolate, O-ethyl-S-metoxyethylphosphorochloridethiolate, O-ethyl-S-ethoxyethylphosphorochloridethiolate, O-ethyl-S-n-propoxyethylphosphorochloride thiolate, O-ethyl-S-isopropoxyethylphosphorochloride thiolate, and O-ethyl-S-n-butoxyethylphosphorochloridethiolate, and the corresponding bromides.

Specific examples of the alcohols and alcoholates of the general formula (III), also used as starting materials in process variant (a), are 2,2,2-trifluoroethanol, 2,2,2-trichloroethanol, 1,1,1,3,3,3-hexafluoro-2-propanol, 1,1,1,3,3,3-hexachloro-2-propanol, and 1-ethoxy-2,2,2-trifluoroethanol, as well as the sodium or potassium salts of these alcohols.

If O-methyl-S-n-propylphosphorochloridethiolate and 2,2,2-trifluoroethanol are used as starting materials in process variant (a), the reaction may be illustrated by the following equation:

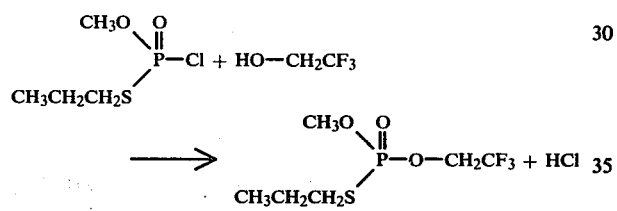

Specific examples of the thiophosphoryl halides of the general formula (IV), used as starting materials in process variant (b), are 0-2,2,2-trifluoroethyl-S-n-propylphosphorochloridethiolate, 0-2,2,2-trichloroethyl-S-n-propylphosphorochloridethiolate, 0-1,1,1,3,3,3-hexafluoro-2-propyl-S-n-propylphosphorochloridethiolate, 0-1,1,1,3,3,3-hexachloro-2-propyl-S-n-propylphosphorochloridethiolate, 0-2,2,2-trichloroethyl-S-n-butylphosphorochloridethiolate, 0-2,2,2-trichloroethyl-S-n-butylphosphorochloridethiolate, 0-1,1,1,3,3,3-hexafluoro-2-propyl-S-n-butylphosphorochloridethiolate, 0-2,2,2-trifluoroethyl-S-isobutylphosphorochloridethiolate, 0-2,2,2-trichloroethyl-S-isobutylphosphorochloridethiolate, 0-1,1,1,3,3,3-hexafluoro-2-propyl-S-sec.-butylphosphorochloridethiolate, 0-2,2,2-trifluoroethyl-S-sec.-butylphosphorochloridethiolate, 0-2,2,2-trichloroethyl-S-sec.-butylphosphorochloridethiolate 0-2,2,2-trifluoroethyl-S-2-methoxyethylphosphorochloridethiolate, 0-2,2,2-trifluoroethyl-S-2-ethoxyethylphosphorochloridethiolate, 0-2,2,2-trichloroethyl-S-2-ethoxyethylphosphorochloridethiolate, 0-1,1,1,3,3,3-hexafluoro-2-propyl-S-2-ethoxyethylphosphorochloridethiolate, 0-2,2,2-trifluoroethyl-S-(2-n-propoxyethyl)phosphorochloridethiolate, 0-2,2,2-trifluoroethyl-S-2-isopropoxyethylphosphorochloridethiolate, 0-2,2,2-trichloroethyl-S-2-isopropoxyethylphosphorochloridethiolate, and 0-2,2,2-trifluoroethyl-S-(2-n-butoxyethyl)phosphorochloridethiolate, and the corresponding bromides.

Examples of the alcohols and alcoholates of the general formula (V), also used as starting materials in process variant (b), are methanol, ethanol and n-propanol, and the sodium or potassium salts of these alcohols.

If 0-2,2,2-trifluoroethyl-S-n-butylphosphochloride thiolate and ethanol are used as starting materials in process variant (b), the reaction may be illustrated by the following equation:

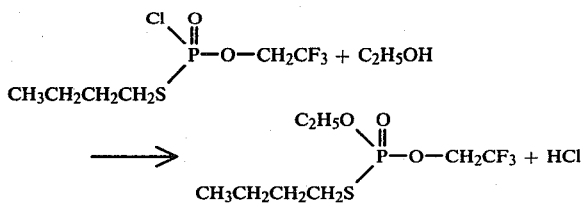

Specific examples of the phosphites of general formula (VI), used as starting materials in process variant (c), are O-methyl-0-2,2,2-trifluoroethyl phosphite, O-methyl-0-2,2,2-trichloroethyl phosphite, O-ethyl-0-1,1,1,3,3,3-trifluoro-2-propyl phosphite, O-ethyl-0-1,1,1,3,3,3-trichloro-2-propyl phosphite, O-ethyl-0-1-ethoxy-2,2,2-trifluoroethyl phosphite, O-n-propyl-0-2,2,2-trifluoroethyl phosphite, O-ethyl-0-2,2,2-trifluoroethyl phosphite, and O-ethyl-0-2,2,2-trichloroethyl phosphite.

Specific examples of the sulfenyl halides of the general formula (VII), also used as starting materials in process variant (c), are 1-propanesulfenyl chloride, 1-butanesulfenyl chloride, isobutanesulfenyl chloride, 2-butanesulfenyl chloride, methoxyethanesulfenyl chloride, ethoxyethanesulfenyl chloride, n-propoxyethanesulfenyl chloride, isopropoxyethanesulfenyl chloride, and n-butoxyethanesulfenyl chloride, as well as the corresponding bromides.

Each of the sulfenyl chlorides or bromides can be easily synthesized by a customary method which comprises reacting the corresponding disulfide with chlorine, bromine, sulfuryl chloride or sulfuryl bromide.

If O-ethyl-0-2,2,2-trichloroethyl phosphite and 1-butanesulfenyl chloride are used as starting materials in process variant (c), the reaction can be illustrated by the following equation:

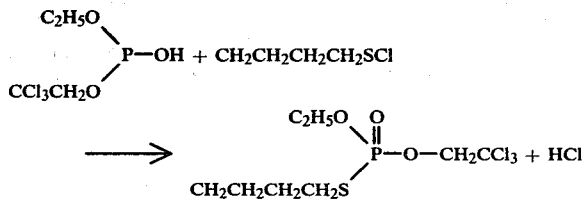

The reaction in process variant (a), (b) or (c) of this invention can be carried out in the presence of an acid-binding agent. Examples of suitable acid-binding agents are the hydroxides, carbonates, bicarbonates and alcoholates of the alkali metals, as well as tertiary amines, such as triethylamine, diethylaniline or pyridine.

Instead of performing the reaction in process variant (a) or (b) in the presence of an acid-binding agent, the product can be obtained in a good yield and purity by reacting the thiophosphoryl halide (II) or (IV) with an alkali metal alcoholate (III) or (IV).

The process of the present invention, whether variant (a), (b) or (c), is carried out preferably using a solvent or diluent. Examples of such solvents or diluents are water and inert organic solvents selected from aliphatic, alicyclic and aromatic hydrocarbons which optionally may be chlorinated, such as hexane, cyclohexane, petroleum ether, ligroin, benzene, toluene, xylene, methylene chloride, chloroform, carbon tetrachloride, ethylene chloride, trichloroethylene and chlorobenzene; ethers, such as diethyl ether, methyl ethyl ether, diisopropyl ether, dibutyl ether, propylene oxide, dioxane and tetrahydrofuran; ketones, such as acetone, methyl ethyl ketone, methyl isopropyl ketone and methyl isobutyl ketone; nitriles, such as acetonitrile, propionitrile and acrylonitrile; alcohols, such as methanol, ethanol, isopropanol, the butanols and ethylene glycol; esters, such as ethyl acetate and amyl acetate; acid amides such as dimethyl formamide and dimethyl acetamide; sulfones and sulfoxides, such as dimethyl sulfoxide and dimethyl sulfone; and organic bases, such as pyridine.

The process of the present invention, whether variant (a), (b) or (c), can be performed in a wide temperature range. In general, the process is carried out at a temperature between $-20°$ C. and the boiling point of the mixture, preferably at a temperature of from $0°$ to $100°$ C. Furthermore, the reaction is preferably carried out at atmospheric pressure, although it can also be performed under an elevated or reduced pressure.

As already mentioned, the compounds according to the present invention are distinguished by an excellent insecticidal, acaricidal and nematocidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine since they are also active against animal parasites, in particular ectoparasites such as parasitic fly larvae.

The active compounds are well tolerated by plants, have a favorable level of toxicity to warm-blooded animals, and can be used for combating arthropod pests, especially insects and acarids, and nematode pests, which are encountered in agriculture, in forestry, in the protection of stored products and of materials, and in the hygiene field. They are active against normally sensitive and resistant species and against all or some stages of development. The abovementioned pests include:

from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallphaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma guadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor, Agriotes spp., Conoderus spp., Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp., The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichlodorus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The active compounds according to the invention can be present in the formulations as a mixture with other active compounds, such as fungicides, insecticides, acaricides, nematocides, herbicides, bird repellants, growth factors, plant nutrients and agents for improving soil structure.

The formulations in general contain from 0.1 to 95 percent by weight of active compound, preferably from 0.5 to 90 percent.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0001 to 20% by weight of active compound, preferably 0.005 to 10% by weight.

The compounds may be employed in a customary manner appropriate for the particular use forms.

In general, 0.03 to 10 kg, preferably 0.3 to 6 kg, of active compound are employed per hectare of soil surface.

The present invention also provides an insecticidal, acaricidal or nematocidal composition containing as active ingredient a compound of the present invention in admixture with a solid or liquefied gaseous diluent or carrier or in admixture with a liquid diluent or carrier containing a surface-active agent.

The present invention also provides a method of combating insects, acarids or nematodes which comprises applying to the insects, acarids or nematodes, or to a habitat thereof, a compound of the present invention alone or in the form of a composition containing as active ingredient a compound of the present invention in admixture with a diluent or carrier.

The present invention further provides crops protected from damage by insects, acarids or nematodes by being grown in areas in which immediately prior to and/or during the time of the growing a compound of the present invention was applied alone or in admixture with a diluent or carrier.

It will be seen that the usual methods of providing a harvested crop may be improved by the present invention.

The following preparative examples are given to illustrate the process for producing the compounds of this invention:

EXAMPLE 1

Variant (a)

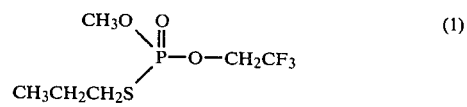

(1)

Triethylamine (11 g) was added dropwise to a mixture of 19 g of O-methyl-S-n-propylphosphorochloride thiolate, 10 g of 2,2,2-trifluoroethanol and 100 ml of toluene at 0° to 10° C. The temperature was gradually raised to 50° to 55° C., and at this temperature, the mixture was stirred for 2 hours.

After allowing the reaction mixture to cool, it was washed with 1% hydrochloric acid, with a 2% aqueous solution of potassium hydroxide and with water in that order, and dried over anhydrous sodium sulfate. The toluene was evaporated, and the residue was distilled under reduced pressure to give 20.2 g of O-methyl-S-n-propyl-O-2,2,2-trifluoroethylphosphorothiolate (b.p. 78°–80° C./0.9 mm Hg; $n_D^{20}=1.4090$).

The compounds in the following table were prepared by analogous methods:

EXAMPLE 3

Variant (c)

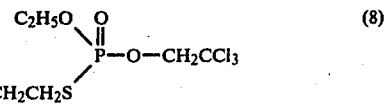

1.78 g of n-butyl disulfide was dissolved in 10 ml of

Table 1

$$\begin{array}{c} R^1O \quad O \quad X \quad Y \\ \diagdown \| \quad | \quad | \\ P-O-CH-C-Y \\ \diagup \quad | \\ R^2S \quad Y \end{array} \quad (I)$$

| Compound | R¹ | R² | X | Y | Physical constants |
|---|---|---|---|---|---|
| 2 | CH₃— | n-C₃H₇— | H | Cl | b.p. 125°–128° C./0.5 mm Hg; $n_D^{20}$ 1.4997 |
| 3 | C₂H₅— | n-C₃H₇— | CF₃— | F | $n_D^{20}$ 1.3898 |
| 4 | C₂H₅— | n-C₃H₇— | CCl₃— | Cl | $n_D^{20}$ 1.5194 |
| 5 | C₂H₅— | n-C₃H₇— | —OC₂H₅ | F | b.p. 90°–92° C./0.8 mm Hg |
| 6 | n-C₃H₇— | n-C₃H₇— | H | F | b.p. 80°–83° C./0.5 mm Hg; $n_D^{20}$ 1.4155 |
| 7 | C₂H₅— | n-C₄H₉— | H | F | b.p. 77°–80° C./0.2 mm Hg; $n_D^{20}$ 1.4242 |
| 8 | C₂H₅— | n-C₄H₉— | H | Cl | b.p. 134°–136° C./0.6 mm Hg; $n_D^{20}$ 1.4885 |
| 9 | C₂H₅— | n-C₄H₉— | CF₃— | F | b.p. 80°–82° C./0.2 mm Hg; $n_D^{20}$ 1.4040 |
| 10 | C₂H₅— | iso-C₄H₉— | H | Cl | $n_D^{20}$ 1.4852 |
| 11 | C₂H₅— | iso-C₄H₉— | H | F | $n_D^{20}$ 1.4165 |
| 12 | C₂H₅— | sec.-C₄H₉— | H | F | b.p. 81°–83° C./0.5 mm Hg; $n_D^{20}$ 1.4200 |
| 13 | C₂H₅— | sec.-C₄H₉— | H | Cl | b.p. 122°–124° C./0.2 mm Hg; $n_D^{20}$ 1.4895 |
| 14 | C₂H₅— | sec.-C₄H₉— | CF₃ | F | b.p. 74°–76° C./0.6 mm Hg; $n_D^{20}$ 1.3965 |
| 15 | C₂H₅— | CH₃OCH₂CH₂— | H | F | b.p. 86°–91° C./0.4 mm Hg; $n_D^{20}$ 1.4227 |
| 16 | C₂H₅— | C₂H₅OCH₂CH₂— | H | F | b.p. 90°–91° C./0.2 mm Hg; $n_D^{20}$ 1.4203 |
| 17 | C₂H₅— | C₂H₅OCH₂CH₂— | H | Cl | b.p. 143°–145° C./1.0 mm Hg; $n_D^{20}$ 1.4901 |
| 18 | C₂H₅— | C₂H₅OCH₂CH₂— | CF₃— | F | b.p. 79°–81° C./0.4 mm Hg; $n_D^{20}$ 1.3975 |
| 19 | C₂H₅— | n-C₃H₇OCH₂CH₂— | H | F | b.p. 98°–102° C./0.3 mm Hg; $n_D^{20}$ 1.4260 |
| 20 | C₂H₅— | iso-C₃H₇OCH₂CH₂— | H | F | b.p. 94°–98° C./0.2 mm Hg; $n_D^{20}$ 1.4269 |
| 21 | C₂H₅— | iso-C₃H₇OCH₂CH₂— | H | Cl | b.p. 127°–132° C./0.2 mm Hg; $n_D^{20}$ 1.4843 |
| 22 | C₂H₅— | n-C₄H₉OCH₂CH₂— | H | F | b.p. 109°–112° C./0.4 mm Hg; $n_D^{20}$ 1.4261 |

EXAMPLE 2

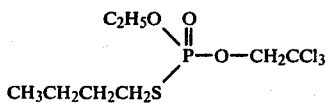

S-n-butylphosphorodichloride thiolate (20.7 g) was dissolved in 150 ml of toluene, and the solution was cooled to −50° C. Then, 14.9 g of 2,2,2-trichloroethanol was added, and, while stirring, 11 g of triethylamine was added at −5° to 0° C. The mixture was allowed to stand overnight at room temperature, and triethylamine hydrochloride was separated by filtration. While stirring, a mixture of 5 g of ethanol and 11 g of triethylamine was added dropwise to the filtrate at 0° to 5° C. After the addition, the temperature was gradually raised to 60° C., and the stirring of the mixture was continued at this temperature for 4 hours. After cooling, the reaction mixture was washed with a 1% aqueous solution of hydrochloric acid, with a 2% aqueous solution of potassium hydroxide and with water, in that order, and dried over anhydrous sodium sulfate. The toluene was evaporated, and the residue was distilled under reduced pressure to give 16.8 g of O-ethyl-S-n-butyl-O-2,2,2-trichloroethylphosphorothiolate. (b.p.=134°–136° C./0.6 mm Hg; $n_D^{20}=1.4885$).

toluene, and 1.35 g of sulfuryl chloride was added dropwise at −5° C. After the addition, the mixture was stirred for 30 minutes at room temperature, and again cooled to −5° C. Then, 4.83 g of O-ethyl-O-(2,2,2-trichloroethyl)-phosphite was added dropwise. After the addition, the mixture was stirred for 30 minutes at room temperature, washed with ice-water, with a 5% aqueous solution of potassium hydroxide and with water, in that order, and dried over anhydrous sodium sulfate. The toluene was evaporated, and the residue was distilled under reduced pressure to give 5.6 g of O-ethyl-S-n-butyl-O-2,2,2-trichloroethylphosphorothiolate as a final product (b.p. 134°–136° C./0.6 mm Hg; $n_D^{20}$:1.4885).

Various pesticidal compositions according to this invention are described in the following examples. The compounds of the present invention are each identified by the number from the preparative examples hereinabove. Parts are by weight.

EXAMPLE 4

A wettable powder was prepared by pulverizing and mixing 15 parts of compound No. 1, 80 parts of a mixture (1:5) of diatomaceous earth and kaolin, and 5 parts of an emulsifier (a polyoxyethylene alkylphenyl ether). This could be diluted with water to a concentration of 0.05% before application by spraying.

EXAMPLE 5

An emulsifiable concentrate was prepared by mixing and stirring 30 parts of compound No. 4, 30 parts of xylene, 30 parts of methylnaphthalene and 10 parts of a polyoxyethylene alkylphenyl ether. This could be diluted with water to a concentration of 0.05% before spraying.

EXAMPLE 6

A dusting agent was prepared by pulverizing and mixing 2 parts of compound No. 7 and 98 parts of a mixture (1:3) of talc and clay. This could be applied by scattering.

EXAMPLE 7

A dusting agent was prepared by pulverizing and mixing 1.5 parts of compound No. 10, 0.5 part of isopropyl hydrogen phosphate (PAP), and 98 parts of a mixture (1:3) of talc and clay.

EXAMPLE 8

10 parts of compound No. 15, 10 parts of bentonite, 78 parts of a mixture (1:3) of talc and clay, and 2 parts of lignin sulfonate were mixed. 25 parts of water were added to the mixture. The whole was mixed thoroughly and then processed with an extrusion granulator into granules of 20 to 40 mesh, which were dried at 40°–50° C.

EXAMPLE 9

95 parts of clay powder having a particle size distribution of 0.2 to 2 mm were placed in a rotary mixer. During rotation, there was sprayed over the particles a solution of 5 parts of compound No. 16 in an organic solvent, thereby wetting them uniformly. Then, drying at 40° to 50° C. was effected in order to form granules.

EXAMPLE 10

An oil preparation was prepared by mixing and stirring 0.5 part of compound No. 20, 20 parts of a high-boiling aromatic compound and 79.5 parts of kerosine.

The insecticidal, acaricidal and nematocidal activity of the compounds of this invention is illustrated by the following examples wherein the compounds according to the present invention are each identified by the number (given in brackets) from the preparative examples hereinabove.

The known comparison compounds are identified as follows:

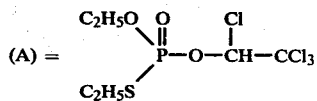

(disclosed in East German Pat. No. 107581)

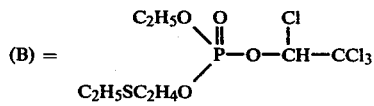

(disclosed in East German Pat. No. 107581)

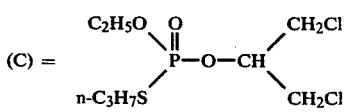

(disclosed in published Japanese patent application 101131/76)

EXAMPLE 11

Test on larvae of *Spodoptera litura*:
Solvent: xylene, 3 parts by weight
Emulsifier: polyoxyethylene alkylphenyl ether, 1 part by weight To form a suitable preparation of an active compound, 1 part by weight of the active compound was mixed with the above amount of the solvent containing the above amount of the emulsifier, and the mixture was diluted with water to a predetermined concentration.

Sweet-potato leaves were dipped in an aqueous formulation containing a predetermined concentration of the active compound. After drying the leaves in air, they were placed in a Petri dish 9 cm in diameter. Then, 10 thirdinstar larvae of *Spodoptera litura* were released into the Petri dish. The dish was placed in a constant-temperature chamber at 28° C. Twenty-four hours later, the number of dead larvae were examined, and the kill ratio was calculated. The results are shown in Table 2.

Table 2

| Compound | Kill ratio (%) at a concentration of active ingredient (ppm) of | | |
|---|---|---|---|
| | 1000 | 300 | 100 |
| (1) | 100 | 100 | |
| (2) | 100 | 100 | |
| (4) | 100 | 100 | 100 |
| (21) | 100 | 100 | |
| (A) | 0 | | |
| (B) | 0 | | |
| (C) | 0 | | |

EXAMPLE 12

Test on *Callosobruchus chinensis*

A filter paper was spread in a Petri dish having a diameter of 9 cm. One milliliter of an aqueous formulation containing a predetermined concentration of the active compound (the formulation having been prepared as in Example 11) was placed in the dish. Twenty specimens of *Callosobruchus chinensis* were placed in the Petri dish, and the dish was put into a constant-temperature chamber at 28° C. After 24 hours the kill ratio was determined.

The results are shown in Table 3.

Table 3

| Compound | Kill ratio (%) at a concentration of the active ingredient (ppm) of | | |
|---|---|---|---|
| | 1000 | 100 | 10 |
| (1) | 100 | 100 | 100 |
| (2) | 100 | 100 | 100 |
| (3) | 100 | 100 | 100 |
| (4) | 100 | 100 | |
| (5) | 100 | 100 | 100 |
| (6) | 100 | 100 | 100 |
| (7) | 100 | 100 | 100 |
| (8) | 100 | 100 | |
| (9) | 100 | 100 | |
| (10) | 100 | 100 | |
| (11) | 100 | 100 | 100 |
| (12) | 100 | 100 | 100 |
| (13) | 100 | 100 | 100 |
| (14) | 100 | 100 | 100 |
| (15) | 100 | 100 | |
| (16) | 100 | 100 | 100 |
| (17) | 100 | 100 | |
| (18) | 100 | 100 | 100 |
| (19) | 100 | 100 | 100 |

Table 3-continued

| Compound | Kill ratio (%) at a concentration of the active ingredient (ppm) of | | |
|---|---|---|---|
| | 1000 | 100 | 10 |
| (20) | 100 | 100 | 100 |
| (21) | 100 | 100 | |
| (22) | 100 | 100 | 100 |
| (A) | 100 | 0 | 0 |
| (B) | 100 | 0 | 0 |
| (C) | 100 | 0 | 0 |

EXAMPLE 13

Test on *Nephotettix cincticeps* having resistance to organophosphorus preparations Rice plants each about 10 cm in height were planted in pots each 12 cm in diameter. Onto the rice plants was applied an aqueous preparation containing a predetermined concentration of the active compound (the formulation having been prepared as in Example) at a rate of 10 ml per pot. After drying the applied preparation, the pots were capped with wire-gauze cages each 7 cm in diameter and 14 cm in height, into which 30 female imagos of *Nephotettix cincticeps* having resistance to organophosphorus agents were released. The pots were then placed in a constant-temperature chamber. Twenty-four hours later, the numbers of dead insects were examined, and the kill ratio was calculated. The results are shown in Table 4.

Table 4

| Compound | Kill ratio (%) at a concentration of the active ingredient (ppm) of | | |
|---|---|---|---|
| | 1000 | 100 | 10 |
| (1) | 100 | 100 | |
| (2) | 100 | 100 | |
| (3) | 100 | 100 | |
| (4) | 100 | 100 | |
| (5) | 100 | 100 | 100 |
| (6) | 100 | 100 | 100 |
| (7) | 100 | 100 | |
| (8) | 100 | 100 | |
| (10) | 100 | 100 | |
| (11) | 100 | 100 | |
| (12) | 100 | 100 | 100 |
| (13) | 100 | 100 | 100 |
| (14) | 100 | 100 | |
| (15) | 100 | 100 | |
| (16) | 100 | 100 | |
| (17) | 100 | 100 | |
| (18) | 100 | 100 | 100 |
| (19) | 100 | 100 | |
| (20) | 100 | 100 | |
| (21) | 100 | 100 | |
| (22) | 100 | 100 | |
| (A) | 0 | | |
| (B) | 0 | | |
| (C) | 0 | | |

EXAMPLE 14

Test on housefly (*Musca domestica*)

A filter paper was spread in a Petri dish having a diameter of 9 cm, and 1 ml of an aqueous preparation having a predetermined concentration of the active compound (which preparation was produced as in Example 11) was placed in the dish. Ten female imagos of *Musca domestica* having resistance to organophosphorus agents were placed into the dish. The dish was put into a constant-temperature chamber at 28° C. Twenty four hours later, the number of dead flies was examined, and the kill ratio was calculated. The results are shown in Table 5.

Table 5

| Compound | Kill ratio (%) at a concentration of the active ingredient (ppm) of | |
|---|---|---|
| | 1000 | 100 |
| (1) | 100 | 100 |
| (2) | 100 | 100 |
| (3) | 100 | 100 |
| (5) | 100 | 100 |
| (6) | 100 | 100 |
| (9) | 100 | 100 |
| (12) | 100 | 100 |
| (13) | 100 | 100 |
| (14) | 100 | 100 |
| (16) | 100 | 100 |
| (18) | 100 | 100 |
| (20) | 100 | 100 |
| (A) | 0 | |
| (B) | 0 | |
| (C) | 0 | |

EXAMPLE 15

Test on *Tetranychus telarius* (spray test)

50 to 100 imagos of *Tetranychus telarius* were placed on the leaves of kidney bean plants at the two-leaf stage cultivated in pots each 9 cm in diameter. Two days after the infestation, an aqueous preparation having a predetermined concentration of the active compound (the preparation having been formulated as in Example 11) was sprayed over the leaves at a rate of 20 ml per pot. Then, the pots were put in a greenhouse. Ten days later, the control effect was evaluated and expressed on the following scale:

3 = 0% survival
2 = more than 0% but less than 5% survival
1 = 5 to 50% survival
0 = more than 50% survival.

The results are given below in Table 6.

Table 6

| Compound | Control effect at a concentration of the active ingredient (ppm) of | | |
|---|---|---|---|
| | 1000 | 300 | 100 |
| (4) | 3 | 3 | 3 |
| (13) | 3 | 3 | 3 |
| (15) | 3 | 3 | 3 |
| (17) | 3 | 3 | |
| (19) | 3 | 3 | 3 |
| (20) | 3 | 3 | 3 |
| (21) | 3 | 3 | |
| (22) | 3 | 3 | |
| (A) | 0 | | |
| (B) | 0 | | |
| (C) | 0 | | |

EXAMPLE 16

Test on *Tetranychus telarius* (irrigation test)

50 to 100 imagos of *Tetranychus telarius* were placed on the leaves of kidney bean plants at the two-leaf stage cultivated in pots each 9 cm in diameter. Two days later, an aqueous preparation having a predetermined concentration of the active compound (the preparation having been made as in Example 11) was applied to the roots of the kidney bean plants at a rate of 20 ml per pot. Then, the pots were placed in a greenhouse. Ten days later, the control effect was evaluated and expressed on the following scale:

3=0% survival
2=more than 0% but less than 5% survival
1=5 to 50% survival
0=more than 50% survival The results are given below in Table 7.

Table 7

| Compound | Control effect at a concentration of the active ingredient (ppm) of | | |
|---|---|---|---|
| | 1000 | 300 | 100 |
| (5) | 3 | 3 | |
| (16) | 3 | 3 | 3 |
| (A) | 0 | | |
| (B) | 0 | | |
| (C) | 0 | | |

EXAMPLE 17

Test on *Blatella germanica*

A filter paper was spread in a Petri dish having a diameter of 9 cm. One milliliter of an aqueous preparation having a predetermined concentration of the active compound (which preparation was produced as in Example 11) was placed in the dish. Ten imagos of *Blatella germanica* were admitted into the dish which was then placed in a constant-temperature chamber at 28° C. Twenty-four hours later, the number of dead insects was examined, and the kill ratio was calculated. The results are shown in Table 8.

Table 8

| Compound | Kill ratio (%) at a concentration of the active ingredient (ppm) of | |
|---|---|---|
| | 1000 | 100 |
| (1) | 100 | 100 |
| (2) | 100 | 100 |
| (3) | 100 | 100 |
| (5) | 100 | 100 |
| (6) | 100 | 100 |
| (12) | 100 | 100 |
| (13) | 100 | 100 |
| (14) | 100 | 100 |
| (15) | 100 | 100 |
| (16) | 100 | 100 |
| (17) | 100 | 100 |
| (18) | 100 | 100 |
| (19) | 100 | 100 |
| (20) | 100 | 100 |
| (21) | 100 | 100 |
| (22) | 100 | 100 |
| (A) | 0 | |
| (B) | 0 | |
| (C) | 0 | |

EXAMPLE 18

Test on the larvae of *Culex tritaeniorhynchus*

In a high-skirted Petri dish with a diameter of 9 cm were placed 100 ml of an aqueous preparation containing a predetermined concentration of the active compounds (which preparation was produced as in Example 11. Twenty-five fourth-instar larvae of *Culex tritaeniorhynchus* were released into the dish, and the dish was put into a constant-temperature chamber at 28° C. Twenty-four hours later, the number of dead insects was examined, and the kill ratio was calculated. The results are shown in Table 9.

Table 9

| Compound | Kill ratio (%) at a concentration of the active ingredient (ppm) of | |
|---|---|---|
| | 1 | 0.1 |
| (13) | 100 | 100 |
| (14) | 100 | 100 |
| (21) | 100 | 100 |
| (A) | 0 | |
| (B) | 0 | |
| (C) | 0 | |

EXAMPLE 19

Test on *Meloidogyne incognita acrita*

An active-compound preparation was prepared by pulverizing and mixing 2 parts by weight of the active compound and 98 parts by weight of talc.

The active compound, processed as above, was added to soil infested by *Meloidogyne incognita acrita* in such amounts as to provide a concentration of 50 ppm, 25 ppm 10 ppm and 5 ppm, respectively. The soil and active compound were mixed uniformly by stirring and then charged into pots each of 0.0002 are. In the treated soil were sown about 20 seeds of tomato (variety: KURIHARA) per pot. The tomato seeds were cultivated in a greenhouse. Four weeks later, the grown roots were pulled out without damaging them, and the degree of injury of 10 selected roots was evaluated based on the following ratings to determine a root-knot index:

Degree of injury

0=no root-knot formation (perfect control)
1=slight root-knot formation
3=much root-knot formation
4=most root-knot formation (corresponding to non-treatment)

$$\text{Root-knot index} = \frac{\Sigma \text{ (rating} \times \text{number of roots)}}{\left(\begin{array}{c}\text{total number of}\\ \text{examined roots}\end{array}\right) \times 4} \times 100$$

From above, the following control effect was obtained:

Control effect =

$$\frac{\left(\begin{array}{c}\text{root-knot index of}\\ \text{untreated plot}\end{array}\right) - \left(\begin{array}{c}\text{root-knot index}\\ \text{of treated plot}\end{array}\right)}{\text{root-knot index of untreated plot}} \times 100$$

A control effect of 100% means a perfect control. The results are shown in Table 10.

Table 10

| Compound | Control effect (%) at a concentration of the active ingredient (ppm) of | | | |
|---|---|---|---|---|
| | 50 | 25 | 10 | 5 |
| (1) | 100 | 100 | 100 | |
| (2) | 100 | 100 | 100 | |
| (3) | 100 | 100 | 100 | |
| (4) | 100 | 100 | | |
| (5) | 100 | 100 | 100 | |
| (6) | 100 | 100 | | |
| (7) | 100 | 100 | 100 | 100 |
| (8) | 100 | 100 | 100 | |
| (9) | 100 | 100 | | |

Table 10-continued

| Compound | Control effect (%) at a concentration of the active ingredient (ppm) of | | | |
|---|---|---|---|---|
| | 50 | 25 | 10 | 5 |
| (10) | 100 | 100 | 100 | |
| (11) | 100 | 100 | 100 | |
| (12) | 100 | 100 | 100 | 100 |
| (13) | 100 | 100 | 100 | 100 |
| (14) | 100 | 100 | 100 | 100 |
| (15) | 100 | 100 | | |
| (16) | 100 | 100 | 100 | 100 |
| (17) | 100 | 100 | 100 | 100 |
| (18) | 100 | 100 | 100 | |
| (19) | 100 | 100 | | |
| (20) | 100 | 100 | 100 | |
| (21) | 100 | 100 | 100 | |
| (22) | 100 | 100 | | |
| (A) | 0 | | | |
| (B) | 0 | | | |
| (C) | 0 | | | |

It will be appreciated that the instant specification and claims are set forth by way of illustration and not limitation, and that various modifications and changes may be made without departing from the spirit and scope of the present invention.

What we claim is:

1. An O,S-dialkyl-O-haloalkylphosphorothiolate of the formula

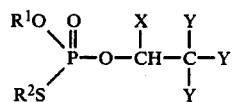

in which
R$^1$ is alkyl with 1–8 carbon atoms,
R$^2$ is alkyl with 1–8 carbon atoms or alkoxyalkyl with 2–8 carbon atoms,
X is trichloromethyl, trifluoromethyl or alkoxy with 1–8 carbon atoms, with the proviso that X can also be hydrogen if R$^2$ is alkyl with 4–8 carbon atoms or alkoxyalkyl with 2–8 carbon atoms, and
Y is chlorine or fluorine.

2. An ester according to claim 1, in which
R$^1$ is alkyl with 1–3 carbon atoms,
R$^2$ is alkyl with 3 or 4 carbon atoms or alkoxyalkyl with 3–6 carbon atoms, and
X is trichloromethyl, trifluoromethyl or alkoxy with 1–4 carbon atoms, with the proviso that X can also be hydrogen if R$^2$ is alkyl with 4 carbon atoms or alkoxyalkyl with 3–6 carbon atoms.

3. An ester according to claim 1, wherein such ester is O-ethyl-S-n-propyl-O-1,1,1,3,3,3-hexafluoro-2-propylphosphorothiolate of the formula

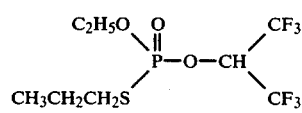

4. An ester according to claim 1, wherein such ester is O-ethyl-S-n-propyl-O-1,1,1,3,3,3-hexachloro-2-propylphosphorothiolate of the formula

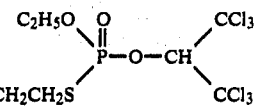

5. An ester according to claim 1, wherein such ester is O-ethyl-S-n-butyl-O-2,2,2-trifluoroethylphosphorothiolate of the formula

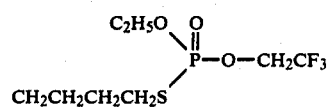

6. An ester according to claim 1, wherein such ester is O-ethyl-S-n-butyl-O-2,2,2-trichloroethylphosphorothiolate of the formula

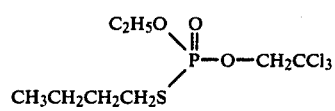

7. An ester according to claim 1, wherein such ester is O-ethyl-S-sec-butyl-O-2,2,2-trifluoroethylphosphorothiolate of the formula

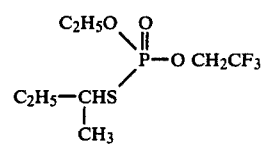

8. An ester according to claim 1, wherein such ester is O-ethyl-S-sec-butyl-O-2,2,2-trichloroethylphosphorothiolate of the formula

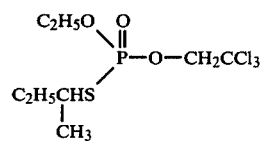

9. An ester according to claim 1, wherein such ester is O-ethyl-S-sec-butyl-O-1,1,1,3,3,3-hexafluoro-2-propylphosphorothiolate of the formula

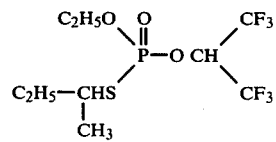

10. An ester according to claim 1, wherein such ester is O-ethyl-S-2-ethoxyethyl-O-2,2,2-trifluoroethylphosphorothiolate of the formula

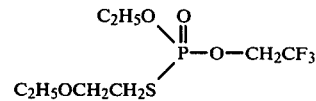

11. An ester according to claim 1, wherein such ester is O-ethyl-S-2-ethoxyethyl-O-2,2,2-trichloroethylphosphorothiolate of the formula

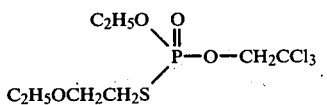

12. An insecticidal, acaricidal or nematocidal composition containing as active ingredient an insecticidally, acaricidally or nematocidally effective amount of an ester according to claim 1 in admixture with a diluent.

13. A method of combating insects, acarids or nematodes which comprises applying to the insects, acarids or nematodes, or to a habitat therof, an insecticidally, acaricidally or nematocidally effective amount of an ester according to claim 1.

14. The method according to claim 13 in which said compound is
O-ethyl-S-n-propyl-O-1,1,1,3,3,3-hexafluoro-2-propylphosphorothiolate,
O-ethyl-S-n-propyl-O-1,1,1,3,3,3-hexachloro-2-propylphosphorothiolate,
O-ethyl-S-n-butyl-O-2,2,2-trifluoroethylphosphorothiolate,
O-ethyl-S-n-butyl-O-2,2,2-trichloroethylphosphorothiolate,
O-ethyl-S-sec-butyl-O-2,2,2-trifluoroethylphosphorothiolate,
O-ethyl-S-sec-butyl-O-2,2,2-trichloroethylphosphorothiolate,
O-ethyl-S-sec-butyl-O-1,1,1,3,3,3-hexafluoro-2-propylphosphorothiolate,
O-ethyl-S-2-ethoxyethyl-O-2,2,2-trifluoroethylphosphorothiolate, or
O-ethyl-S-2-ethoxyethyl-O-2,2,2-trichloroethylphosphorothiolate.

* * * * *